US012275992B2

(12) United States Patent
Cao et al.

(10) Patent No.: US 12,275,992 B2
(45) Date of Patent: *Apr. 15, 2025

(54) CHARACTERIZATION OF MOLECULES IN NANOFLUIDICS

(71) Applicant: Bionano Genomics, Inc., San Diego, CA (US)

(72) Inventors: Han Cao, San Diego, CA (US); Alex R. Hastie, San Diego, CA (US); Ernest Tsz-Tsun Lam, San Diego, CA (US)

(73) Assignee: Bionano Genomics, Inc., San Diego, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/741,708

(22) Filed: May 11, 2022

(65) Prior Publication Data

US 2022/0340973 A1 Oct. 27, 2022

Related U.S. Application Data

(63) Continuation of application No. 16/887,679, filed on May 29, 2020, now Pat. No. 11,359,244, which is a continuation of application No. 15/795,847, filed on Oct. 27, 2017, now Pat. No. 10,669,586, which is a continuation of application No. 14/768,422, filed as application No. PCT/US2014/017226 on Feb. 19, 2014, now Pat. No. 9,809,855.

(60) Provisional application No. 61/767,219, filed on Feb. 20, 2013.

(51) Int. Cl.
*C12Q 1/6809* (2018.01)
*B01L 3/00* (2006.01)
*C12Q 1/6883* (2018.01)
*G01N 33/50* (2006.01)
*G16B 30/00* (2019.01)
*G16B 30/10* (2019.01)

(52) U.S. Cl.
CPC .......... *C12Q 1/6883* (2013.01); *B01L 3/5027* (2013.01); *C12Q 1/6809* (2013.01); *G01N 33/5091* (2013.01); *G16B 30/00* (2019.02); *G16B 30/10* (2019.02); *B01L 2200/10* (2013.01); *B01L 2300/0627* (2013.01); *C12Q 2600/166* (2013.01)

(58) Field of Classification Search
CPC ............... C12Q 1/6883; C12Q 1/6809; C12Q 2600/166; C12Q 2565/1025; C12Q 2565/629; B01L 3/5027; B01L 2200/10; B01L 2300/0627; G01N 33/5091; G16B 30/00; G16B 30/10
See application file for complete search history.

(56) References Cited

U.S. PATENT DOCUMENTS

| | | |
|---|---|---|
| 8,628,919 B2 | 1/2014 | Xiao et al. |
| 8,722,327 B2 | 5/2014 | Cao et al. |
| 9,310,376 B2 | 4/2016 | Cao et al. |
| 9,809,855 B2 | 11/2017 | Cao et al. |
| 10,000,804 B2 | 6/2018 | Cao et al. |
| 2003/0104428 A1 | 6/2003 | Branton et al. |
| 2004/0197843 A1 | 10/2004 | Chou et al. |
| 2006/0063184 A1 | 3/2006 | Felix et al. |
| 2008/0242556 A1 | 10/2008 | Cao et al. |
| 2009/0305273 A1 | 12/2009 | Cao et al. |
| 2010/0285082 A1 | 11/2010 | Fernandez |
| 2011/0117577 A1 | 5/2011 | Reboud et al. |
| 2011/0171634 A1 | 7/2011 | Xiao et al. |
| 2011/0229888 A1 | 9/2011 | Hengen et al. |
| 2011/0296903 A1 | 12/2011 | Cao et al. |
| 2011/0306504 A1 | 12/2011 | Xiao et al. |
| 2012/0095697 A1 | 4/2012 | Halpern et al. |
| 2012/0097835 A1 | 4/2012 | Sharonov |
| 2012/0100600 A1 | 4/2012 | Slepnev |
| 2012/0108920 A1 | 5/2012 | Bly et al. |
| 2012/0237936 A1 | 9/2012 | Xiao et al. |
| 2012/0244635 A1 | 9/2012 | Austin et al. |
| 2013/0034546 A1 | 2/2013 | Rava et al. |
| 2013/0036860 A1 | 3/2013 | Xiao et al. |
| 2013/0055817 A1 | 3/2013 | Maeda et al. |
| 2013/0072386 A1 | 3/2013 | Xiao et al. |
| 2013/0085681 A1 | 4/2013 | Deciu et al. |
| 2013/0103320 A1 | 4/2013 | Dzakula et al. |
| 2013/0150253 A1 | 6/2013 | Deciu et al. |
| 2013/0261983 A1 | 10/2013 | Dzakula et al. |
| 2013/0309666 A1 | 11/2013 | Deciu et al. |
| 2013/0325360 A1 | 12/2013 | Deciu et al. |
| 2013/0338933 A1 | 12/2013 | Deciu et al. |
| 2014/0014497 A1 | 1/2014 | Druz et al. |
| 2014/0099642 A1 | 4/2014 | Jiang et al. |
| 2016/0046992 A1 | 2/2016 | Cao et al. |

FOREIGN PATENT DOCUMENTS

| | | |
|---|---|---|
| WO | WO2008079169 | 7/2008 |
| WO | WO2008121828 | 10/2008 |
| WO | WO2009149362 | 12/2009 |
| WO | WO2010002883 | 1/2010 |
| WO | WO2010059731 | 5/2010 |

(Continued)

OTHER PUBLICATIONS

U.S. Appl. No. 61/713,862, filed Oct. 15, 2012, Saghbini et al.

(Continued)

*Primary Examiner* — Narayan K Bhat

(74) *Attorney, Agent, or Firm* — Dickinson Wright PLLC

(57) ABSTRACT

Systems are provided for detecting and quantitating short nucleic acid molecules.

21 Claims, 11 Drawing Sheets

(56) References Cited

FOREIGN PATENT DOCUMENTS

| WO | WO2010135323 | 11/2010 | | |
|---|---|---|---|---|
| WO | WO2011038327 | 3/2011 | | |
| WO | WO2011050147 | 4/2011 | | |
| WO | WO-2011109762 A1 * | 9/2011 | ......... | B01L 3/50273 |
| WO | WO2012054735 | 4/2012 | | |
| WO | WO2012108920 | 8/2012 | | |
| WO | WO2013000100 | 1/2013 | | |
| WO | WO2013036860 | 3/2013 | | |
| WO | WO2013052907 | 4/2013 | | |
| WO | WO2013052913 | 4/2013 | | |
| WO | WO2013055817 | 4/2013 | | |
| WO | WO2013109981 | 7/2013 | | |
| WO | WO2013166517 | 11/2013 | | |
| WO | WO2013177086 | 11/2013 | | |
| WO | WO2013192562 | 12/2013 | | |
| WO | WO2014014497 | 1/2014 | | |
| WO | WO2014123822 | 8/2014 | | |
| WO | WO2014130589 | 8/2014 | | |

OTHER PUBLICATIONS

U.S. Appl. No. 61/734,327, filed Dec. 6, 2012, Saghbini et al.
Chao & Tammi, "CNV-seq, a new method to detect copy number variation using high-throughput sequencing," BMC Bioinformatics 2009, 10(80), doi:10.1186/1471-2105-10-80, in 9 pages.
Examination Report dated Apr. 26, 2018 in European Patent Application No. 14753475.4.
Examination Report dated Mar. 7, 2019 in European Patent Application No. 14753475.4.
Extended European Search Report dated Jul. 14, 2016 in European Patent Application No. 14753475.4.
Final Office Action dated Jul. 16, 2019 in U.S. Appl. No. 15/795,847.
Final Office Action dated Oct. 23, 2019 in U.S. Appl. No. 15/117,689.
International Preliminary Report on Patentability dated Aug. 30, 2016 in PCT Application No. PCT/US2015/017356.
International Preliminary Report on Patentability dated Apr. 10, 2015 in PCT Application No. PCT/US2014/017226.
International Search Report and Written Opinion dated Jun. 10, 2015 in PCT Application No. PCT/US2015/017356.
International Search Report and Written Opinion dated May 30, 2014 in PCT Application No. PCT/US2014/017226.
Jensen et al., "Detection of Microdeletion 22q11.2 in a Fetus by Next-Generation Sequencing of Maternal Plasma," Clinical Chemistry 2012, 58(7), 1148-1151.
Jensen et al., "High-Throughput Massively Parallel Sequencing for Fetal Aneuploidy Detection from Maternal Plasma," PLoS One 2013, 8(3), e57381, in 8 pages.
Kidd et al., "Mapping and sequencing of structural variation from eight human genomes," Nature 2008, 453, 56-64.
Lam et al., "Genome mapping on nanochannel arrays for structural variation analysis and sequence assembly," Nature Biotechnology 2012, 30(8), 771-776.
Mazloom et al., "Noninvasive prenatal detection of sex chromosomal aneuploidies by sequencing circulating cell-free DNA from maternal plasma," Prenatal Diagnosis 2013, 33, 591-597.
Nord et al., "Accurate and exact CNV identification from targeted high-throughput sequence data," BMC Genomics 2011, 12(184), 1-10.

Non-Final Office Action dated Oct. 26, 2016 in U.S. Appl. No. 14/768,422.
Non-Final Office Action dated Dec. 11, 2018 in U.S. Appl. No. 15/795,847.
Non-Final Office Action dated Feb. 27, 2019 in U.S. Appl. No. 15/117,689.
Non-Final Office Action dated Nov. 9, 2021 in U.S. Appl. No. 16/887,679.
Notification of Reasons for Refusal dated Oct. 16, 2018 in Japanese Patent Application No. 2015-558929.
Notification of Reasons for Refusal dated Jan. 30, 2018 in Japanese Patent Application No. 2015-558929.
Notice of Allowance dated Jul. 6, 2017 in U.S. Appl. No. 14/768,422.
Notice of Allowance dated Apr. 26, 2019 in Japanese Patent Application No. 2015-558929.
Notice of Allowance dated Jan. 23, 2020 in U.S. Appl. No. 15/795,847.
Notice of Allowance dated Apr. 17, 2020 in Chinese Patent Application No. 201480009730.6.
Notice of Allowance dated Apr. 30, 2020 in Chinese Patent Application No. 201580016272.3.
Notice of Allowance dated May 18, 2020 in European Patent Application No. 14753475.4.
Notice of Allowance dated Jul. 28, 2020 in U.S. Appl. No. 15/117,689.
Notice of Allowance dated Jul. 6, 2021 in Japanese Patent Application No. 2019-110164.
Notice of Allowance dated Mar. 7, 2022 in U.S. Appl. No. 16/887,679.
Office Action dated Oct. 24, 2016 in Chinese Patent Application No. 201480009730.6.
Office Action dated Jun. 14, 2018 in Chinese Patent Application No. 201480009730.6.
Office Action dated Sep. 20, 2017 in Chinese Patent Application No. 201480009730.6.
Office Action dated Mar. 29, 2019 in Chinese Patent Application No. 201580016272.3.
Office Action dated Jan. 2, 2020 in Chinese Patent Application No. 201580016272.3.
Office Action dated Jan. 27, 2020 in Canadian Patent Application No. 2,901,460.
Office Action dated Jul. 21, 2020 in Japanese Patent Application No. 2019-110164.
Office Action dated Feb. 5, 2021 in Canadian Patent Application No. 2,901,460.
Office Action dated Feb. 7, 2022 in Canadian Patent Application No. 2,901,460.
Oldridge et al., "Optimizing copy number variation analysis using genome-wide short sequence oligonucleotide arrays," Nucleic Acids Research 2010, 38(10), 3275-3286.
Schouten et al., "Platform comparisons for identification of breast cancers with a BRCA-like copy number profile," Breast Cancer Research and Treatment 2013, 139, 317-327.
Stavis et al., "Single-molecule mobility and spectral measurements in submicrometer fluidic channels," Journal of Applied Physics 2005, 98(044903), in 5 pages.
Yahya-Graison et al., "Classification of Human Chromosome 21 Gene-Expression Variations in Down Syndrome: Impact on Disease Phenotypes," The American Journal of Human Genetics 2007, 81, 475-491.

* cited by examiner 834 bp 498 bp 233 bp

CHARACTERIZATION OF MOLECULES IN NANOFLUIDICS

CROSS-REFERENCE TO RELATED APPLICATIONS

This application is a continuation of U.S. patent application Ser. No. 16/887,679, filed on May 29, 2020, which is a continuation of U.S. patent application Ser. No. 15/795,847, filed on Oct. 27, 2017 and now U.S. Pat. No. 10,669,586, which is a continuation of U.S. patent application Ser. No. 14/768,422, having a 371(c) date of Aug. 17, 2015 and now U.S. Pat. No. 9,809,855, which is the national phase of International Application PCT/US2014/017226 filed on Feb. 19, 2014, which claims the benefit of U.S. Provisional Application No. 61/767,219, filed on Feb. 20, 2013, each of which is hereby incorporated by reference in its entirety.

SUMMARY

According to some embodiments herein, a method of characterizing a sample is provided. The method can comprise labeling a plurality of sample molecules with at least a first label, wherein the sample molecules comprise polynucleotide sequences of a first genomic fragment or fragments of interest, and wherein first genomic fragment or fragments of interest correspond to a possibly abnormal genomic region of the sample. The method can comprise providing a plurality of labeled reference molecules, wherein the reference molecules comprise polynucleotide sequences of a reference genomic fragment or fragments, and wherein the reference genomic fragment or fragments are known not to correspond to the possibly abnormal genomic region. As used herein "correspond to a possibly abnormal genomic region" and variations of this root term includes genomic fragments that overlap with or are encompassed by an abnormal chromosomal region, including, but not limited to a duplication, deletion, inversion, translocation, and or aneuploid chromosome or fragment thereof. As such, a genomic fragment or fragment can correspond to an abnormal genomic region that is either present (e.g. a duplication) or absent (e.g. a deletion, for example if the genomic fragment would be encompassed by or overlap with the deleted region). The method can comprise translocating the plurality of labeled sample molecules and the plurality of labeled reference molecules though a fluidic channel. The method can comprise detecting signals from the labeled sample molecules so as to ascertain at least a first pattern or plurality of patterns characteristic of the first genomic fragment or fragments of interest; and a second pattern or plurality of patterns characteristic of the reference genomic fragment or fragments. The method can comprise correlating signals ascertaining the first pattern or plurality of patterns to signals ascertaining the second pattern or plurality of patterns. In some embodiments, labeling comprises labeling the sample molecules with a first label, and wherein the reference molecules comprise a second label, in which the first label is configured to produce the first pattern or plurality of patterns, and in which the second label is configured to produce the second pattern or plurality of patterns, and in which the first label and the second label are different from each other. In some embodiments, labeling comprises labeling with a first label, in which the first pattern or plurality of patterns and the second pattern or plurality of patterns each comprise the first label, and in which the first pattern or plurality of patterns and second pattern or plurality of patterns are different from each other. In some embodiments, the method further comprised labeling the reference molecules so as to produce the labeled reference molecules, wherein the labeled reference molecules comprise the second pattern or plurality of patterns. In some embodiments, the labeled reference molecules and sample molecules are from the sample. In some embodiments, the labeled reference molecules are from a different tissue of the same organism as the sample. In some embodiments, the labeled reference molecules and sample molecules are from different organisms. In some embodiments, the signal from the labeled reference molecules comprises an electronically or optically stored value or set of values. In some embodiments, the method further comprises labeling a second plurality of sample molecules from a second sample with at least the first label, wherein the second plurality of sample molecules comprise polynucleotide sequences of the first genomic fragment or fragments of interest, wherein the second plurality of sample molecules is known to not correspond to the chromosomal abnormality, and translocating the second plurality of sample molecules through the fluidic channel, and detecting signals from the labeled sample molecules so as to ascertain at least the first pattern or plurality of patterns characteristic of the first genomic fragment or fragments of interest; and the second pattern or plurality of patterns characteristic of the reference genomic fragment or fragments. In some embodiments, the method further comprises aligning the positions of the patterns to positions of patterns in a reference genome. In some embodiments, the sample molecules are from a sample comprising the possible genomic abnormality, and the reference genomic fragment or fragments comprise the first chromosome or fragment thereof, in which the reference genomic fragments are from a second sample known to not comprise the genomic abnormality. In some embodiments, the first genomic fragment or fragments of interest comprise a sex chromosome or a least one fragment thereof, and the reference genomic fragment or fragments comprise an autosome or at least one fragment thereof. In some embodiments, the first genomic fragment or fragments of interest comprise a first autosome or at least one fragment thereof, selected from the group consisting of: human chromosome 21, human chromosome 13, human chromosome 14, human chromosome 15, human chromosome 16, human chromosome 18, and human chromosome 22, and fragments thereof, and the reference genomic fragment or fragments comprise a second autosome or at least one fragment thereof, wherein the second autosome or fragment thereof is different than the first autosome or fragment thereof. In some embodiments, correlating signals comprises using the ratio (K) between the signal arising from a plurality of labeled sample molecules or portions thereof (S1, S2 . . . Sn) and the signal arising from the reference (C): $K1=S1/C$, $K2=S2/C$ . . . $Kn=Sn/C$. In some embodiments, the first label comprises at least one of a fluorescent label, a radioactive label, a magnetic label, or a non-optical label. In some embodiments, the second label comprises at least one of a fluorescent label, a radioactive label, a magnetic label, or a non-optical label. In some embodiments, labeling comprises nicking one strand of a double-stranded DNA at a first sequence motif with a nicking endonuclease; and labeling the DNA. In some embodiments, the method further comprises repairing at least some of the nicks on the DNA. In some embodiments, the nicks are not repaired. In some embodiments, the label comprises a transcriptional terminator. In some embodiments, labeling with the first label comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase. In some embodiments, the method further comprises labeling the sample molecule with a non-sequence-specific label. The non-sequence specific label can be different from the first label and the second label. In some embodiments, the possible abnormal genomic region comprises at least one of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy tetraploidy, or sex chromosome aneuploidy. In some embodiments, the genetic abnormality comprises at least one of a trisomy or monosomy.

According to some embodiments herein, a method of characterizing a sample is provided. The method can comprise labeling a plurality of sequence-specific locations on a polynucleotide sequence of a sample molecule. The method can comprise linearizing at least a portion of the sample molecule in a fluidic channel. The method can comprise quantifying a signal from the labels on the sample molecule. The method can comprise comparing a quantity of the signal from the sample molecule to a quantity of signal from a reference molecule. The method can comprise determining a presence or absence of a genetic abnormality in the sample DNA when the quantity of the signal from the sample molecule differs from the quantity of the signal arising from the reference molecule. In some embodiments, the sample molecule and the reference molecule are from the same organism. In some embodiments, the sample molecule and the reference molecule are from different tissues of the same organism. In some embodiments, the sample molecule and the reference molecule are from different organisms. In some embodiments, the signal from the quantity of signal from the reference molecule comprises an electronically or optically stored value or set of values. In some embodiments, the sample molecule comprises a DNA. In some embodiments, the genetic abnormality comprises at least one of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy tetraploidy, or sex chromosome aneuploidy. In some embodiments, the genetic abnormality comprises at least one of a trisomy or monosomy. In some embodiments, labeling comprises labeling the polynucleotide with at least one of a fluorescent label, a radioactive label, a magnetic label, or a non-optical label. In some embodiments, labeling comprises: nicking one strand of a double-stranded DNA at a first sequence motif with a nicking endonuclease; and labeling the DNA. In some embodiments, labeling, further comprises repairing at least some of the nicks on the first DNA. In some embodiments, the nicks are not repaired. In some embodiments, the label comprises a transcriptional terminator. In some embodiments, labeling comprises tagging at least one sequence motif of the sample molecules with a DNA binding entity selected from the group consisting of: a non-cutting restriction enzyme, a zinc finger protein, an antibody, a transcription factor, a transcription activator like domain, a DNA binding protein, a polyamide, a triple helix forming oligonucleotide, and a peptide nucleic acid, and a methyltransferase. In some embodiments, labeling with the first label comprises tagging at least one sequence motif of the sample molecules with a methyltransferase.

According to some embodiments herein, a method of characterizing a sample is provided. The method can comprise labeling sample nucleic acid molecules. The method can comprise translocating the labeled sample nucleic acid molecules through a fluidic nanochannel, wherein the fluidic nanochannel is configured to elongate at least a portion of the sample nucleic acid molecules, and wherein the fluidic nanochannel has a length of at least 10 nm and a cross-sectional diameter of less than 1000 nm. The method can comprise detecting signals arising from the sample nucleic acid molecules in the fluidic channels. The method can comprise determining the positions of the labels on the sample nucleic acid molecules. The method can comprise aligning the positions of the labels on the sample nucleic acid molecules to the position of labels in a reference genome, wherein the reference genome is obtained from a second sample from the same organism as the sample molecules.

In some embodiments, the fluidic nanochannel of any of the methods herein comprises a channel having a length of at least 10 nm and a cross-section diameter of less than 5000 nm. In some embodiments, the fluidic channel comprises a nanochannel. In some embodiments, the fluidic channel is disposed parallel to a surface of a substrate. In some embodiments. In some embodiments, the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

In some embodiments, the sample of any of the methods herein is selected from the group consisting of a bacteria, a virion, a DNA molecule, an RNA molecule, a nucleic acid polymer, a protein, a peptide, and a polysaccharide. In some embodiments, the sample of any of the methods herein is derived from maternal blood, and wherein the reference molecule is derived from a maternal sample other than blood. In some embodiments, the sample of any of the methods herein comprises a nucleotide, and wherein the at least two labels are located at either end of a zone of interest in the nucleotide. In some embodiments, the sample of any of the methods herein comprises circulating fetal cells, circulating tumor cells, or body fluids or tissues.

In some embodiments, any of the methods herein comprises optical inspection comprising determining the physical count, the intensity, the wavelength, or the size of the labels. In some embodiments, any of the methods herein comprise optical inspection comprising determining the length of at least one labeled region in the sample. In some embodiments, any of the methods herein, further comprise determining the signals arising from a pool comprising the sample or portions of the sample.

In some embodiments, any of the methods herein comprises using the ratio (K) between the signal arising from a plurality of samples or sample portions (S1, S2 . . . Sn) and the signal arising from the reference (C): $K1=S1/C$, $K2=S2/C$ . . . $Kn=Sn/C$ In some embodiments, a difference between K1 and Kn is used to identify the presence of a fetal sample. In some embodiments, a difference between K1 and Kn is used to identify the presence of DNA from a tumor or other cancer source. In some embodiments, a difference between K1 and Kn is used to determine the presence of a genetic abnormality in the sample. In some embodiments, the genetic abnormality is aneuploidy. In some embodiments, the genetic abnormality is a translocation, addition, amplification, transversion, or inversion.

In some embodiments, any of the methods herein comprises a reference derived from a known diploid or haploid chromosome. In some embodiments, any of the methods herein comprises correlating signals from the sample with the population distribution from a metagenomic or microbiome study. In some embodiments, any of the methods herein comprises generating a histogram distribution to reflect coverage depth for the sample.

In some embodiments, a system for characterizing a sample is provided. The system can comprise one or more regions for labeling sample molecules with at least two labels. The system can comprise a fluidic channel for translocating the labeled sample molecules, in which the fluidic channel is configured to elongate at least a portion of the sample molecule, and in which the fluidic channel has a length of at least 10 nm and a cross-sectional diameter of less than 5000 nm. The system can comprise a device for detecting signals arising from the labeled samples in the fluidic channels.

In some embodiments, a system for characterizing a sample is provided. The system can comprise one or more regions for labeling sample nucleic acid molecules. The system can comprise a fluidic nanochannel for translocating the labeled sample nucleic acid molecules, in which the fluidic nanochannel is configured to elongate at least a portion of the sample nucleic acid molecules, and in which the fluidic nanochannel has a length of at least 10 nm and a cross-sectional diameter of less than 1000 nm. The system can comprise a device for detecting signals arising from the sample nucleic acid molecules in the fluidic channels.

In some embodiments a system for characterizing a sample is provided. The system can comprise a region for labeling a plurality of sequence-specific locations on a sample DNA. The system can comprise a region for linearizing at least a portion of the sample DNA. The system can comprise a device for quantifying the signal arising from the labels on the sample DNA.

In some embodiments, a system for characterizing a sample is provided. The system can comprise a means for labeling sample molecules with at least two labels. The system can comprise a means for linearizing the labeled sample molecules. The system can comprise a means for detecting signals arising from the labeled samples in the fluidic channels.

In some embodiments, a system for characterizing a sample is provided. The system can comprise a means for labeling sample nucleic acid molecules. The system can comprise a means for linearizing the labeled sample nucleic acid molecules. The system can comprise a means for detecting signals arising from the sample nucleic acid molecules in the fluidic channels.

In some embodiments, a system for characterizing a sample is provided. The system can comprise a means for labeling a plurality of sequence-specific locations on a sample DNA. The system can comprise a means for linearizing at least a portion of the sample DNA. The system can comprise a means for quantifying the signal arising from the labels on the sample DNA.

In some embodiments, any of the systems as described herein can characterize a sample selected from the group consisting of a bacteria, a virion, a DNA molecule, an RNA molecule, a nucleic acid polymer, a protein, a peptide, and a polysaccharide. In some embodiments, any of the systems as described herein can characterize a sample derived from maternal blood, and wherein the reference molecule is derived from a maternal sample other than blood. In some embodiments, any of the systems as described herein can characterize a sample comprising a nucleotide, and wherein the at least two labels are located at either end of a zone of interest in the nucleotide. In some embodiments, any of the systems as described herein can characterize a sample comprising circulating fetal cells, circulating tumor cells, or body fluids or tissues.

In some embodiments, any of the systems as described herein can comprise a label selected from the group consisting of a fluorescent label, a radioactive label, a magnetic label, or a combination thereof. In some embodiments, any of the systems as described herein can be configured for optical inspection, wherein optical inspection comprises determining the physical count, the intensity, the wavelength, or the size of the labels. In some embodiments, the optical inspection comprises determining the length of at least one labeled region in the sample. In some embodiments, any of the systems as described herein can be configured for correlating the signals, in which correlating the signals comprises determining the signals arising from a pool of samples or a pool of portions of a sample. Some embodiments, any of the systems as described herein can be configured for correlating the signals, in which correlating the signals comprises using the ratio (K) between the signal arising from a plurality of samples or sample portions (S1, S2 . . . Sn) and the signal arising from the reference (C): K1=S1/C, K2=S2/C . . . Kn=Sn/C. In some embodiments, a difference between K1 and Kn is used to identify the presence of a fetal sample. In some embodiments, a difference between K1 and Kn is used to identify the presence of DNA from a tumor or other cancer source. In some embodiments, a difference between K1 and Kn is used to determine the presence of a genetic abnormality in the sample. In some embodiments, the genetic abnormality is aneuploidy. In some embodiments, the genetic abnormality is a translocation, addition, amplification, transversion, or inversion.

In some embodiments, any of the systems as described herein can comprise a reference derived from a known diploid or haploid chromosome.

In some embodiments, any of the systems as described herein can correlated the signals from the sample with the population distribution from a metagenomic or microbiome study.

In some embodiments, the fluidic channel any of the systems as described herein comprises a nanochannel. In some embodiments, the fluidic channel of any of the systems as described herein is disposed parallel to a surface of a substrate. In some embodiments, the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

In some embodiments, any of the systems as described herein is configured to generate a histogram distribution to reflect coverage depth for the sample.

In some embodiments a kit for performing any of the methods as described herein is provided.

In some embodiments a kit for using any of the systems as described herein is provided.

BRIEF DESCRIPTION OF THE DRAWINGS

FIGS. 5A-5B show quantitative measurement of small fragment molecules or particles: samples of 6 different known concentrations of each DNA were prepared; used the same loading parameters for all the samples of each DNA; performed 3 scans for each sample; and counted the number of particles in each scan. Initial Results: number of DNAs in the Field of View is linearly concentration dependent; the concentration of an unknown DNA of similar size can be extrapolated and measured; a long range of concentrations can be covered by changing the loading parameters.

DETAILED DESCRIPTION

Figure 1:
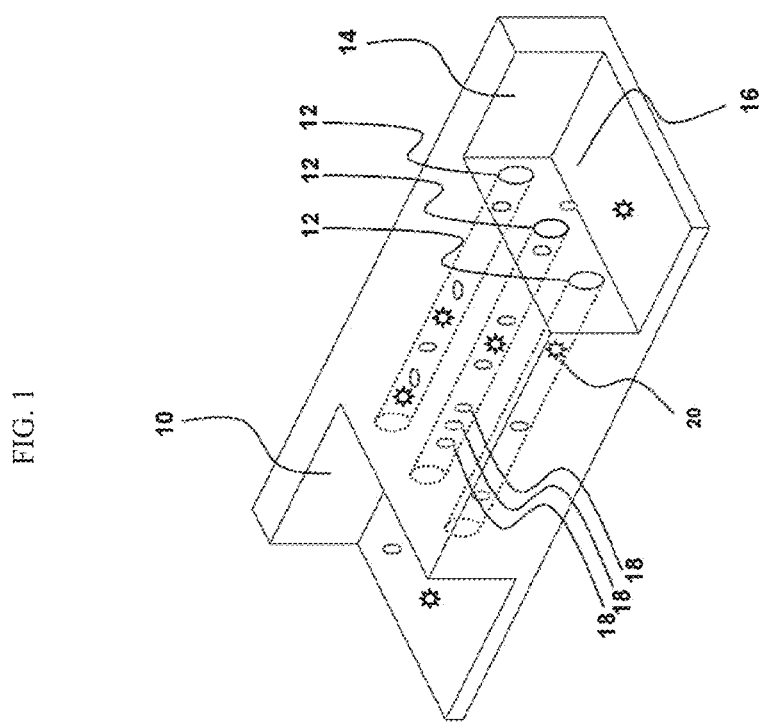
FIG. 1 is a schematic diagram illustrating sample molecules or particles (ovals) and reference or comparative molecules or particles (spheres) flowing through nanofluidic channels, in accordance with some embodiments herein.

The fetus sheds small DNA fragments into the maternal bloodstream. Tumors have also been found to release DNA into the bloodstream. According to some embodiments herein are methods for analyzing polynucleotide fragments such as DNA fragments in blood to detect the presence of circulating polynucleotide or cells from a fetus or tumor.

Also according to some embodiments herein are methods for analyzing fetal DNA in maternal blood to detect genetic abnormalities. In some preferred embodiments, the methods described herein entail the use of a nanofluidic-based single molecule detecting platform to identify genetic abnormalities. Methods and apparatuses in accordance with some embodiments herein have the advantage of analyzing small or large molecules, such as small or large DNA molecules. In some embodiments, a molecule or region of interest is labeled with at least one pattern, and a reference molecule or region of interest is labeled with at least one pattern. The molecules can be linearized in a microfluidic channel, and coverage depth for the molecule or region of interest can be compared to coverage depth for the reference molecule so as to determine copy number of the molecule of interest.

It is estimated that about 3-15% of short DNAs in maternal blood are fetal derived. Described herein are methods of easily detecting and quantitating small molecules, including short DNA fragments, using methods that incorporate fluidics. In some preferred embodiments, the methods comprise quantitating short DNA fragments without sequencing or assembly.

Current prenatal tests involving needle puncture to draw amniotic fluid can lead to miscarriage and other complications. Further, many current cancer detection methods also involve invasive procedures, such as biopsies. According to some embodiments herein, a non-invasive method of prenatal testing is provided. In some embodiments, the method is for testing blood. In some embodiments, the method only tests a blood sample, and does not test a sample from other tissues.

Also described herein are methods of detecting and tracking larger molecules, including longer DNA fragments, to their source using methods that incorporate fluidics. For example, in some embodiments, DNA fragments are tracked back to a tumor or other source of cancer. In some preferred embodiments, the methods are used to track DNA fragments to their source in order to identify or characterize a genetic abnormality.

In a preferred embodiment, circulating DNA from a maternal blood sample is analyzed to identify and quantify fetal DNA relative to the maternal genome. In some embodiments, this information is used to determine prenatal genomic health status (such as trisomy 21) without invasive tests. Examples of suitable oligos for use in an assay for detecting aneuploidy are provided in the HSA21 oligoarray described in Yahya-Graison et al., Classification of Human Chromosome 21 Gene-Expression Variations in Down Syndrome: Impact on Disease Phenotypes, Am J Hum Genet 2007, 81(3): 475-491, which is hereby incorporated by reference in its entirety.

In some embodiments, a sample of interest is compared to a reference sample. In some embodiments, the sample of interest is derived from a maternal blood sample. In some of these embodiments, the reference sample is a maternal sample from a source other than blood. In some embodiments, the maternal reference sample includes polynucleotides such as DNA isolated from a diploid tissue other than blood. In some embodiments, the maternal reference sample comprises a buccal sample, a saliva sample, a urine sample, a sputum sample, or a tear sample. For example, in some embodiments, trisomy 21 is detected in a maternal blood sample compared to a maternal buccal sample.

In some embodiments, the sample of interest is enriched for fetal nucleic acids prior to performing the methods described herein. For example, in some embodiments, fetal cells are enriched using a fetal cell specific marker that can be pulled down by an antibody. In some embodiments, the sample of interest undergoes size fractionation. However, any method of enrichment known to one of skill in the art can be used.

In some embodiments, the sample of interest is derived from a tumor cell or suspected tumor cell, or a tissue in fluid communication with a tumor cell (for example, blood). In some embodiments, the reference sample is sample from a healthy cell. In some embodiments, the reference sample is from a healthy cell of the same organism as the tumor cell or suspect tumor cell. In some embodiments, the reference sample is selected from a tissue that has little to no likelihood of comprising a tumor cell or nucleic acid from the tumor cell.

As one of skill in the art will recognize, the sample of interest may include nucleic acids from a variety of sources. In some embodiments, the sample of interest comprises a bacteria or virion derived from an environmental sample, animal or plant tissue, blood, or other body fluid. In some embodiments, DNA fragments are used to detect chromosomal abnormalities or cancer genomes.

As one of skill in the art will recognize, the methods described herein can be used to prepare and analyze DNA from circulating fetal or tumor cells. For example, in some embodiments, cells are lysed to release DNA of interest prior to analysis.

In some embodiments, an entire genome is assayed or analyzed. In some embodiments, only a portion of a genome is assayed or analyzed. In some embodiments, an entire chromosome is assayed or analyzed. In some embodiments, only a portion of a chromosome is assayed or analyzed. In some embodiments, an entire gene is analyzed. In some embodiments, only a portion of a gene is assayed or analyzed.

The signals described herein can include any suitable signal, including optical signals, fluorescent signals, non-optical signals, radiative signals, electrical signals, magnetic signals, chemical signals, or any combination thereof. In some embodiments, signals are generated by an electron spin resonance molecule, a fluorescent molecule, a chemiluminescent molecule, a radioisotope, an enzyme substrate, a biotin molecule, an avidin molecule, an electrical charged transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a nanowire, a hapten, an antibody, an antibody fragment, a lipid, or a combination thereof.

In some embodiments, signals are generated by using one or more excitation sources to induce fluorescence, chemoluminescence, phosphorescence, bioluminescence, or any combination thereof. Suitable excitation sources include lasers, visible light sources, sources of infrared light, sources of ultraviolet light, or any combination thereof.

Figure 3C:
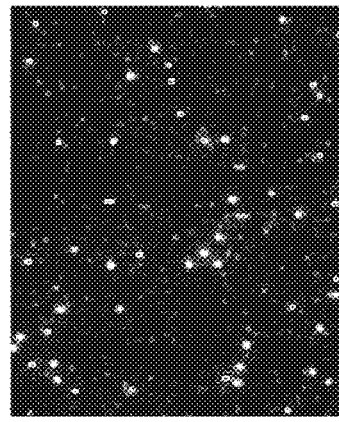
FIGS. 3A-3C are a series of images illustrating small double stranded DNA fragments with known sizes (233 bp, 498 bp, and 834 bp) that were generated by PCR, fluorescently stained, flowed, and imaged in individual nanofluidic channels.
Figure 3B:
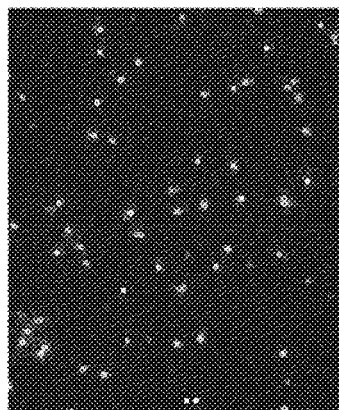
Figure 3A:
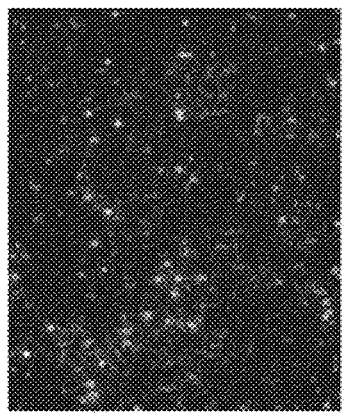
Figure 3E:
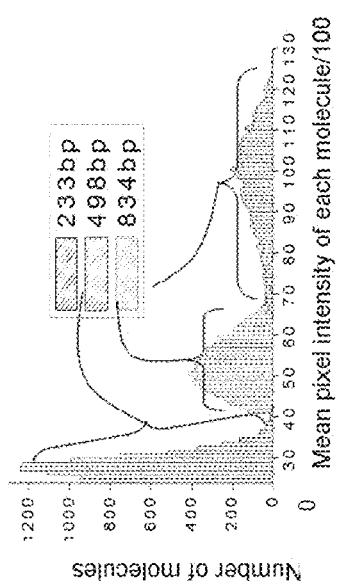
FIGS. 3D and 3E show the same double stranded DNA fragments that were mixed together, flowed, and imaged in the same nanofluidic channel. The fluorescent signals were plotted in a histogram (FIG. 3E).
Figure 3D:
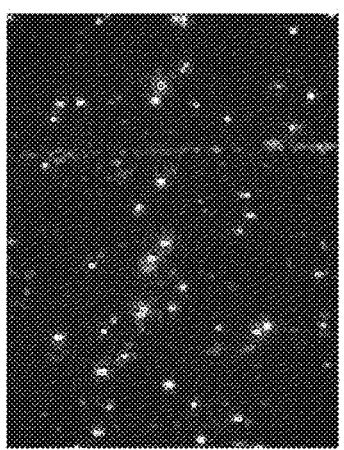
Figure 4A:
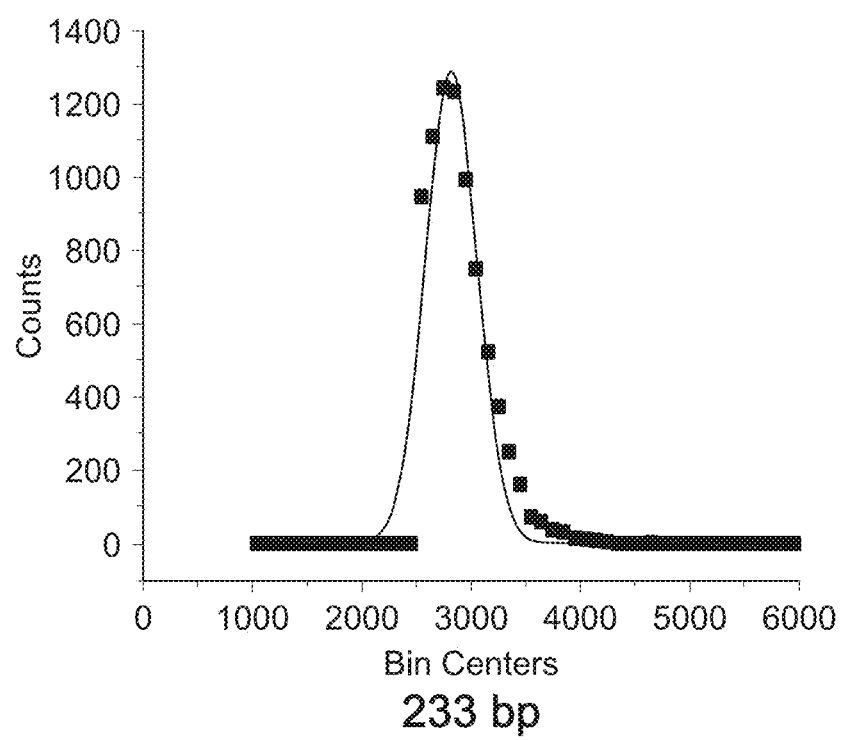
FIGS. 4A-D are a series of graphs illustrating Gaussian curves depicting the photons emitted from individually labeled DNA molecules with known sizes (233 bp, 498 bp, and 834 bp). Total counts and intensity were linearly proportional to mass and/or molecule size. Unknown molecule sizes and quantities can be extrapolated by this method within a linear dynamic range.
Figure 4B:
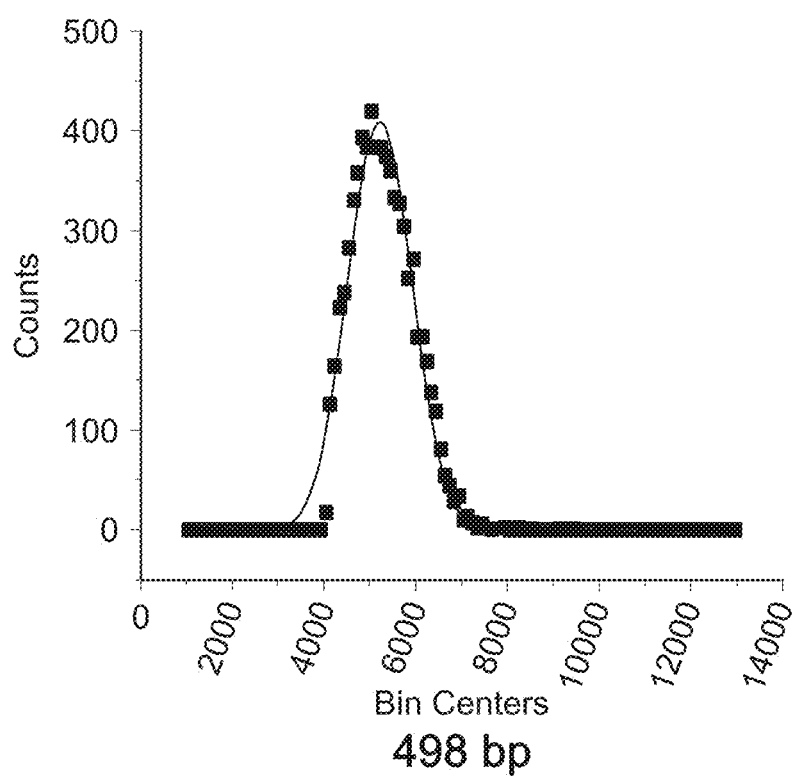
Figure 4C:
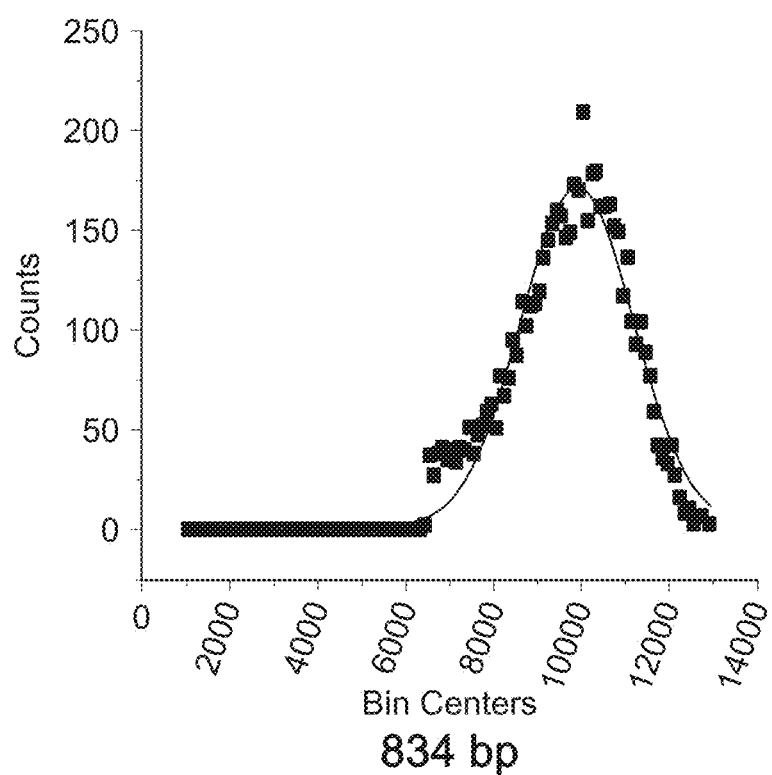
Figure 4D:
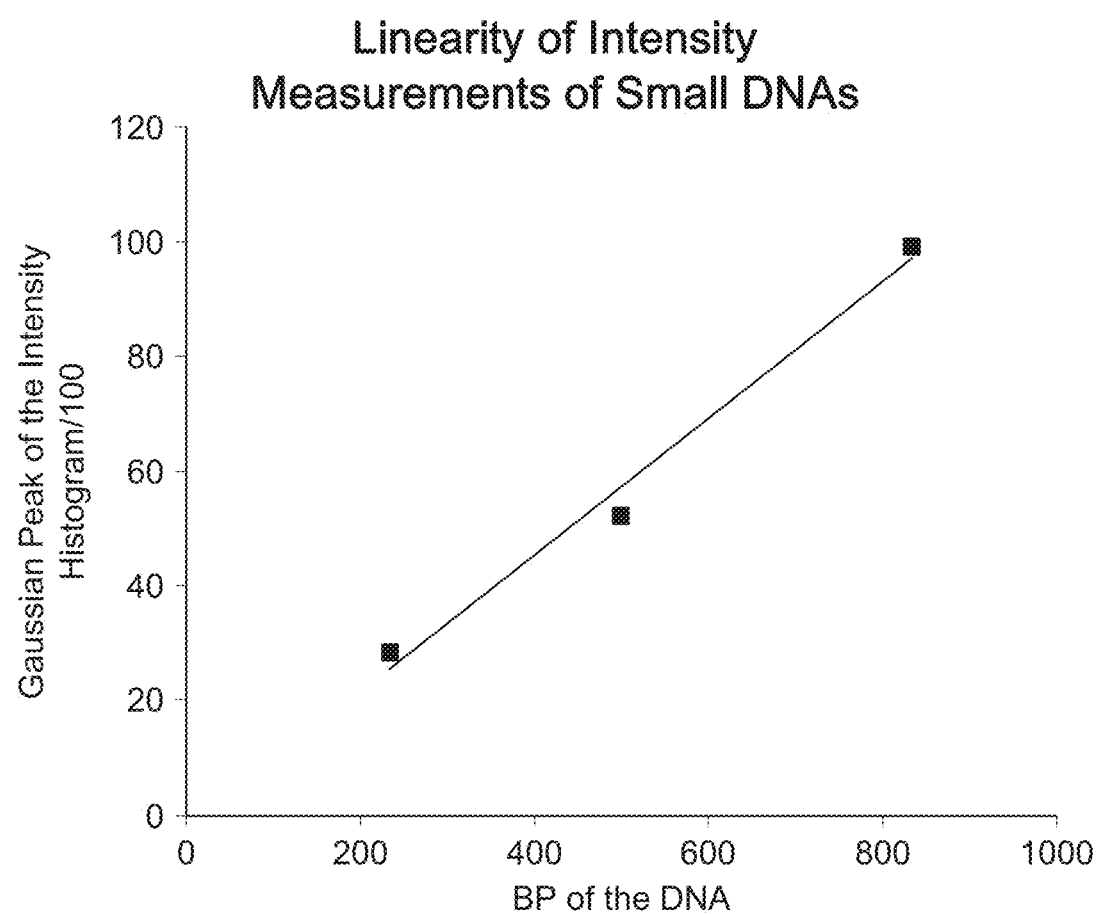
Figure 5B:
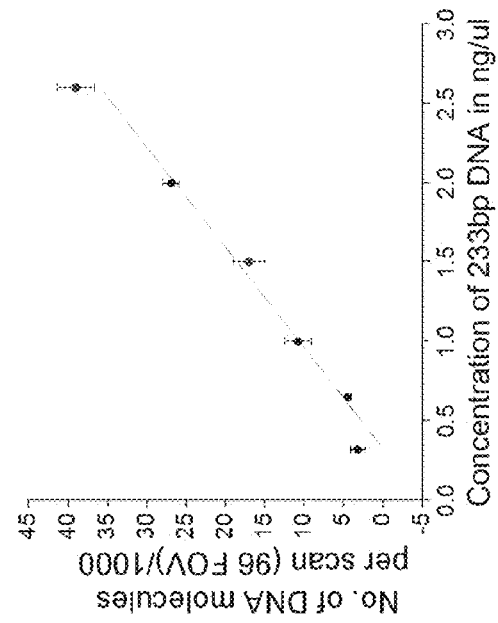
FIGS. 5A-5B are a series of scatter plots illustrating the extrapolation of unknown molecule sizes and quantities within a linear dynamic range using the information from FIG. 4.
Figure 5A:
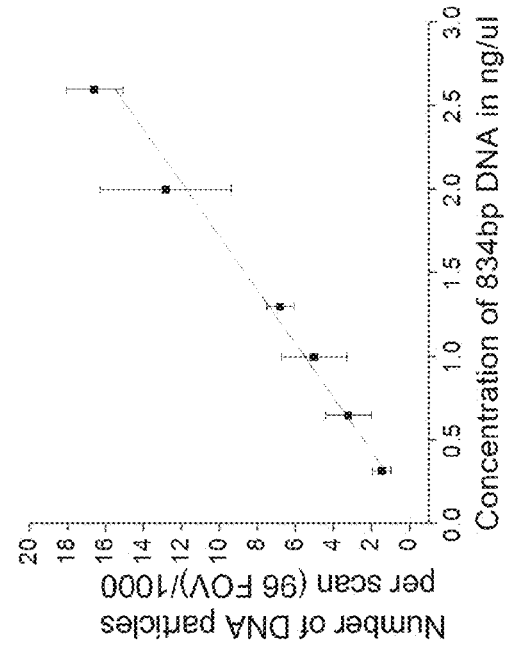
Figure 6:
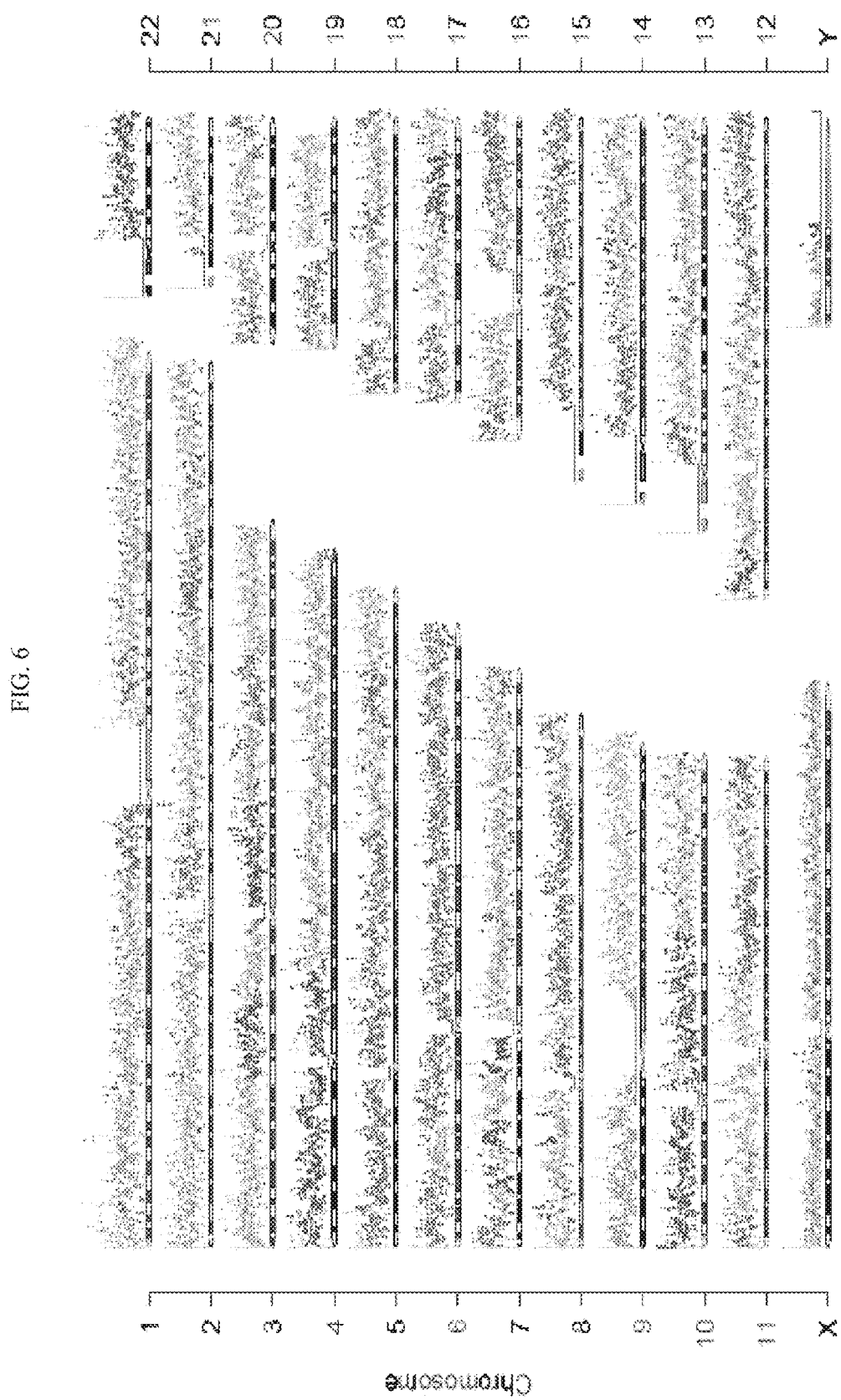
FIG. 6 is a histogram illustrating genomic DNA fragments plotted against a reference genome (human genome version 19). The y-axis shows coverage depth for specific chromosomal regions. A uniform distribution throughout the genome was observed, except for regions without sequence information (such as the centromeres and telomeres).

In some embodiments, the detection of nucleotides or associated signals (for example, fluorophores) is quantitative. In some embodiments, the length of a nucleotide is quantified. In some embodiments, the size of a molecule is quantified. In some embodiments, the strength of a signal correlates with the length of a molecule. For example, as shown in FIG. 3A, longer DNA molecules can generate stronger signals than shorter DNA molecules. In some embodiments, the strength of a signal correlates to the amount of DNA in a sample or fluidic channel.

In some embodiments, samples are analyzed for copy number variation, for example, as described in U.S. Patent Publication No. 20130034546, which is hereby incorporated by reference in its entirety.

The quantity of particular molecules, such as DNA fragments derived from different chromosomes, can be quantitatively measured in the methods provided herein. In some embodiments, the amount of genomic DNA derived from a diploid autosomal chromosome is observed to be twice as much as that derived from a haploid sex chromosome. In some embodiments, the quantity of such fragments reflects the copy number of a source chromosomes. In some embodiments, two or three color labels are used.

In some embodiments, chromosome derived fragments are detected, and a relative ratio is used to identify aneuploidy. In some embodiments, the copy number of a nucleotide is calculated using the ratios $K1=S1/C$ and $K2=S2/C$, wherein K1 is the ratio of the signal for a first sample to a control sample, and K2 is the ratio of the signal for a second sample to the control sample. It is contemplated that the copy number from the reference sample is an integer, and that the difference between K1 and K2 can indicate an abnormality in one of the samples of interest. In some embodiments, the abnormality is detected by comparing the ratio for a particular sample to the average ratio from a plurality of samples. The methods further contemplate that the control genomic sequence includes separate portions whose total length per genome is known, wherein the sequence of interest comprises separate portions whose length per normal gene is known, and wherein a significant difference between K1 and K2 indicates a genetic abnormality in the genome. In some embodiments, the nucleotide sequence of interest can relate to a trisomy-linked chromosome, wherein the control genomic sequence is from a chromosome other than the trisomy-linked chromosome, and wherein a K1/K2 ratio of approximately 2:3 or 3:2 indicates a trisomic genotype. In some embodiments, the nucleotide sequence of interest comprises a deletion of a portion of a genome. In some embodiments, the nucleotide sequence of interest comprises a repeating sequence. As such, a copy number of repeating sequence can be determined according to some embodiments herein. In some embodiments, the first sample comprises maternal blood (which, without being limited by any one theory, may include fetal nucleic acids), and the second sample comprises maternal tissue other than blood (preferably a tissue with little to no likelihood of comprising fetal nucleic acids).

In some embodiments, digital counting detection is performed. In some embodiments, digital counting detection is performed on particles (such as beads), bacteria, or virion particles. As one of skill in the art will recognize, the methods described herein can apply to a variety of targets that can be uniquely labeled. In some embodiments, digital karyotyping is performed. For example, in some embodiments, digital karyotyping is performed for a chromosome with potential aneuploidy of interest. The methods described herein can be used to detect any chromosomal variation of interest, including translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy tetraploidy, and sex chromosome abnormalities, including but not limited to XO, XXY, XYY, and XXX.

In some embodiments, methods are provided herein in which the methods are sensitive enough to detect "short" fragments that are on the order of tens to hundreds of nucleotides in length. In some embodiments, the sample molecules as described herein comprise polynucleotide "short" fragments. For example, in some embodiments, the polynucleotide fragments are about 10, 15, 20, 25, 30, 35, 40, 45, 50, 55, 60, 65, 70, 75, 80, 85, 90, 95, or 100 nucleotides in length. In some embodiments, the polynucleotide fragments are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nucleotides in length. In some embodiments, the molecules of interest are fragments of less than about 1000, 950, 900, 850, 800, 750, 700, 650, 600, 550, 500, 450, 400, 350, 300, 250, 200, 150, 100, or 50 nucleotides in length. In some embodiments, the fragments are double-stranded. In some embodiments, the fragments comprise DNA. In some embodiments, the fragments comprise RNA. In some embodiments, the fragments comprise DNA hybridized to RNA. In some embodiments, the sensitivity is about as high as detecting a single fluorophore associated with a target fragment.

In some embodiments, the nucleotides of interest are fragments of at least about 500 nucleotides in length, for example about 500, 600, 700, 800, 900, 1000, 1100, 1200, 1300, 1400, 1500, 1600, 1700, 1800, 1900, or 2000 nucleotides in length, including ranges between any two of the listed values, for example about 500 to about 2000 nucleotides in length, about 500 to about 1500, about 500 to about 1000, about 500 to about 900, about 500 to about 700, about 700 to about 2000, about 700 to about 1500, about 700 to about 1000, about 700 to about 900, about 1000 to about 2000, about 1000 to about 1500, or about 1500 to about 2000.

Molecules suitable for use in the methods and systems described herein include polymers, double-stranded DNA, single-stranded DNA, RNA, DNA-RNA hybrids, polypeptides, biological molecules, proteins, and the like. Suitable polymers include homopolymers, copolymers, block copolymers, random copolymers, branched copolymers, dendrimers, or any combination thereof.

In some embodiments, the methods described herein are sensitive enough to detect a fetal molecule that constitutes less than about 0.025%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 6%, 7%, 8%, 9%, 10%, 11%, 12%, 13%, 14%, 15%, 20%, or 25% of the total number of molecules in a maternal blood sample.

In some embodiments, labeling is directed to a sequence motif or chemical moiety. Labeling can be carried out using any technique known to one of skill in the art, including chemical or biochemical conjugation. In some embodiments, the labels described herein are bound to a unique sequence motif. In some embodiments, the labels described herein are bound to a chemical moiety. In some of these embodiments, the chemical moiety is related to a specific chromosome.

In some embodiments herein, each label is independently selected from the group consisting of a fluorophore, a quantum dot, a dendrimer, a nanowire, a bead, a hapten, a streptavidin, an avidin, a neutravidin, a biotin, and a reactive group. In some embodiments herein, the first and second labels are independently selected from the group consisting of a fluorophore or a quantum dot. In some embodiments herein, at least one of the labels comprises a non-optical label. In some embodiments, the labeling is carried out with a polymerase. In some embodiments herein, the labeling is carried out with a polymerase in the presence of dNTPs comprising the label. In some embodiments herein, the polymerase has a 5' to 3' exonuclease activity. In some embodiments herein, the polymerase leaves a flap region, and wherein the flap region is removed to restore a ligatable nick prior to the repairing with a ligase. In some embodiments herein, the flap region is removed using the 5' to 3' exonuclease activity of a polymerase under conditions wherein at least one nucleotide is present in limited concentration. In some embodiments herein, the flap region is removed using the 5' to 3' exonuclease activity of a polymerase under conditions wherein at least one nucleotide is omitted from the reaction. In some embodiments herein, the flap region is removed with a flap endonuclease. In some embodiments herein, the labeling is carried out with a polymerase in the presence of at least one species of dNTP. In some embodiments herein, the at least one species of dNTP is a single species of dNTP. In some embodiments herein, a method as described herein further comprises modulating activity of the polymerase by adjusting the temperature, dNTP concentration, cofactor concentration, buffer concentration, or any combination thereof, during labeling. In some embodiments herein, nicking the first motif or the second motif comprising nicking with Nt.BspQI. In some embodiments herein, the a non-sequence-specific label, for example a polynucleotide backbone label is applied in addition to a sequence-specific label or labels as described herein.

In some embodiments, at least one label as described herein comprises a non-optical label. A variety of non-optical labels can be used in conjunction with embodiments herein. In some embodiments a non-optical label comprises an electronic label. Exemplary electronic labels include, but are not limited to molecule with a strong electric charge, for example ions such as a metal ions, charged amino acid side chain, or other cations or anions. An electronic label can be detected, for example, by conductivity (or resistivity) when the label is disposed in a detector. In some embodiments, a nanochannel comprises an electrode configured to determine the presence or absence of an electronic label by determining the conductivity or resistivity of a substance disposed in the channel. In some embodiments, the non-optical label comprises a metal, metal oxide (for example metal oxide), or silicon oxide moiety. In some embodiments, the non-optical label comprises a moiety (for example a nanoparticle) comprising a metal, metal oxide, or other oxide. The presence of a particular metal or oxide moiety can be detected, for example by nuclear magnetic resonance. In some embodiments, the label is configured to release a moiety, for example a proton or an anion, upon a certain condition (e.g. change of pH) and the presence or absence of released moiety is detected.

In some embodiments, two or more labels are different from each other. For example, a first motif can be labeled with a first label so as to generate a first unique pattern, and a second motif that is different from the first motif can be labeled with a second label different from the first label so as to generate a second unique pattern. In some embodiments, two or more labels are the same. For example, a first motif can be labeled with a label, and a second motif that is different from the first motif can also be labeled with the same label so as to generate a unique pattern. In some embodiments, a plurality of probes corresponding to a first chromosome or region of interest are labeled with a first label, and a second plurality of probes corresponding to a second chromosome or region of interest (for example a reference chromosome or region) are labeled with a second label that is different than the first label. As such, labeled sample molecules comprising sequences from the first chromosome or region of interest can be differentiated from sample molecules comprising sequences from the second chromosome or region of interest based on whether they are labeled with the first label or second label.

Nucleotides with reversible terminators can form a first phosphodiester linkage, but prior to reversal of termination, cannot form (or have limited capacity to form) a second phosphodiester linkage. Thus, a nucleotide with a reversible terminator can be incorporated into a polynucleotide (for example at a nick site), but the nucleotide cannot form downstream phosphodiester linkages until the terminator is reversed. Reversal can be performed using techniques known to one skilled in the art. For example, the terminator can be attached to the nucleotide via cleavable linker, which can be cleaved, for example, via electromagnetic radiation. If nick repair is performed using labeled nucleotides comprising a 3' reversible terminator, a single labeled nucleotide can be incorporated into the nick, but the terminator can prevent additional labeled nucleotides from being incorporated into the nick. Accordingly, nick labeling can be limited to one labeled nucleotide per nick. Limiting nick labeling to one label moiety per nick can minimize potential bias from multiple labels being incorporated into the same nick. For example, if approaches are taken to limit labeling to one label moiety per nick, two nicks that are very close together can be resolved based on a relatively strong signal from the label (i.e. the possibility that two labels simply got incorporated into the same nick can be ruled-out). For example, if quantitative estimates of the number of nicks is desired, a one-label-per-nick approach can facilitate direct correlation between strength of label signal and the number of nicks. The label on the nucleotide comprising a reversible terminator can be as described herein. In some embodiments, the nucleotide comprising a reversible terminator comprises a quantum dot. In some embodiments, the nucleotide comprising a reversible terminator comprises a fluorophore. In some embodiments, the nucleotide comprising a reversible terminator comprises a non-optical label.

In some embodiments, a plurality of labels label a single sample molecule. In some embodiments, at least one of the labels comprises a sequence specific label. In some embodiments, at least one of the labels comprises a non-sequence specific label. In some embodiments, at least one label comprises a sequence specific label, and at least one label comprises a non-sequence specific label. In some embodiments, at least one label does not cut one or both strands of DNA. For example, in some embodiments, at least one label is selected from the group consisting of a non-cutting restriction enzyme, a methyltransferase, a zinc finger protein, an antibody, a transcription factor, a DNA binding protein, a hairpin polyamide, a triplex-forming oligodeoxynucleotide, a peptide nucleic acid, or a combination thereof. In some embodiments, neither the sequence specific nor the non-sequence specific label cuts DNA.

In some embodiments, for example if fluorescent labeling is provided, labeling is detected using a sensitive camera. In some embodiments, for example if non-optical labeling is provided, labeling is detected electronically. However, any detection method can be used that is suitable for the corresponding label. The methods described herein can include binding to a fluorescent label, a radioactive label, a magnetic label, or any combination thereof in one or more regions of the molecules described herein. Binding may be accomplished where the label is specifically complementary to a molecule or to at least a portion of a molecule or other region of interest.

In some embodiments, nicking enzymes create sequence-specific nicks that are subsequently labeled, for example using a labeled nucleotide or nucleotide analog. In some embodiment, the nucleotide or analog is fluorescently labeled. In some embodiments, DNA is linearized by confinement in a nanochannel, resulting in uniform linearization and allowing precise and accurate measurement of the distance between nick-labels on DNA molecules comprising a signature pattern. In some embodiments, a second nicking enzyme is used. In some embodiments, the second nicking enzyme is used with a second label color. Exemplary nickases that can be used in accordance with embodiments herein include, but are not limited to Nb.BbvCI; Nb.BsmI; Nb.BsrDI; Nb.BtsI; Nt.AlwI; Nt.BbvCI; Nt.BspQI; Nt.BstNBI; Nt.CviPII and combinations thereof. Examples of nicking agents and protocols are also provided in U.S. Patent Application Publication No. 2011/0171634 and U.S. Patent Application Publication No. 2012/0237936, which are hereby incorporated by reference in their entireties.

In some embodiments, a polynucleotide, for example an RNA or DNA, is labeled by hybridizing a probe to a single strand of the polynucleotide. The probe can be complementary to a strand of the RNA or DNA or a portion thereof. In some embodiments, the probe is complementary to a particular sequence motif. In some embodiments, a plurality of probes is provided so as to be complementary to a plurality of specific sequence motifs, for example at least 2, 3, 4, 5, 6, 7, 8, 9, 10, 20, 30, 40, 50, 60, 70, 80, 90, 100, 200, 300, 400, 500, 600, 700, 800, 900, 1000, 5,000, or 10,000 probes, including ranges between any two of the listed values. In some embodiments, the probe has a random sequence. In some embodiments, a probe with a plurality of random sequences is provided. In some embodiments, a probe includes one or more of an organic fluorophore, quantum dot, dendrimer, nanowires, bead, Au beads, paramagnetic beads, magnetic bead, a radiolabel, polystyrene bead, polyethylene bead, peptide, protein, haptens, antibodies, antigens, streptavidin, avidin, neutravidin, biotin, nucleotide, oligonucleotide, sequence specific binding factors such as engineered restriction enzymes, methyltransferases, zinc finger binding proteins, and the like. In some embodiments, the probe includes a fluorophore-quencher pair. One configuration of the probe can include a fluorophore attached to the first end of the probe, and an appropriate quencher tethered to the second end of the probe. As such, when the probe is unhybridized, the quencher can prevent the fluorophore from fluorescing, while when the probe is hybridized to a target sequence, the probe is linearized, thus distancing the quencher from the fluorophore and permitting the fluorophore to fluoresce when excited by an appropriate wavelength of electromagnetic radiation. In some embodiments, a first probe includes a first fluorophore of a FRET pair, and a second probe includes a second fluorophore of a FRET pair. As such, hybridization of the first probe and the second probe to a single flap, or to a pair of flaps within a FRET radius of each other can permit energy transfer by FRET. In some embodiments, a first probe includes a first fluorophore of a FRET pair, and a label on a nucleotide incorporated to fill a corresponding gap can include second fluorophore of a FRET pair. As such, hybridization of the first probe to a flap, and the labeled nucleotide into the corresponding gap can permit energy transfer by FRET.

In some embodiments, a double-stranded DNA can be labeled by first melting hydrogen bonds between double stands of certain genomic regions to open a so-called D-loop, by increasing temperature or manipulation with organic solvent, and then hybridizing to at least one specific probes with equal or higher affinity to single stranded regions before annealing back to relative stable form. As such, in some embodiments, double-stranded DNA can be labeled by a probe as described herein without nicking or cutting either strand. In some embodiments, a plurality of D-loops can be opened on a single strand. As such, a plurality of probes can be annealed to a particular double-stranded DNA.

In some embodiments, labeling comprises transferring a label to the polynucleotide via a methyltransferase. In some embodiments, the methyltransferase specifically methylates a sequence motif. As such, labeling can comprise transferring a label to a sequence motif by the methyltransferase. Exemplary suitable DNA methyltransferases (MTase) include, but are not limited to, M.BseCI (methylates adenine at N6 within the 5'-ATCGAT-3' sequence), M.TaqI (methylates adenine at N6 within the 5'-TCGA-3' sequence) and M.HhaI (methylates the first cytosine at C5 within the 5'-GCGC-3' sequence). In some embodiments, two or more methyltransferases provide two or more labels, which can be the same or different.

In some embodiments, labeling comprises transferring a label to the polynucleotide via a methyltransferase. In some embodiments, the methyltransferase specifically methylates a sequence motif. As such, labeling can comprise transferring a label to a sequence motif by the methyltransferase. Exemplary suitable DNA methyltransferases (MTase) include, but are not limited to, M.BseCI (methylates adenine at N6 within the 5'-ATCGAT-3' sequence), M.TaqI (methylates adenine at N6 within the 5'-TCGA-3' sequence) and M.HhaI (methylates the first cytosine at C5 within the 5'-GCGC-3' sequence). In some embodiments, two or more methyltransferases provide two or more labels, which can be the same or different.

In some embodiments, the channel comprises a microchannel. In some embodiments, the channel comprises a nanochannel. Suitable fluidic nanochannel segments have a characteristic cross-sectional dimension of less than about 1000 nm, less than about 500 nm, or less than about 200 nm, or less than about 100 nm, or even less than about 50 nm, about 10 nm, about 5 nm, about 2 nm, or even less than about than about 0.5 nm. A fluidic nanochannel segment suitably has a characteristic cross-sectional dimension of less than about twice the radius of gyration of the molecule. In some embodiments, the nanochannel has a characteristic cross-sectional dimension of at least about the persistence length of the molecule. Fluidic nanochannel segments suitable for the present invention have a length of at least about 100 nm, of at least about 500 nm, of at least about 1000 nm, of at least about 2 microns, of at least about 5 microns, of at least about 10 microns, of at least about 1 mm, or even of at least about 10 mm. Fluidic nanochannel segments are, in some embodiments, present at a density of at least 1 fluidic nanochannel segment per cubic centimeter.

Examples of fluidic channels can be found in U.S. Patent Publication No. 2008/0242556, which is incorporated herein by reference in its entirety. In some embodiments, a virion particles or a bacterial cell is assayed. For example, in some embodiments, a bacterial cell is assayed using a microchannel. In some embodiments, the channel allows a cell with a diameter in the range of microns to tens of microns to flow through.

FIG. 1 is a schematic diagram illustrating a fluidic channel arrangement according to some embodiments herein. The arrangement can include a sample input chamber 10. The arrangement can include an array of fluidic channels 12, for example fluidic nanochannels. The arrangement can include a sample output chamber 14. The output chamber can comprise buffer solution 16. The array of nanofluidic channels 12 can be in fluid communication with the input chamber 10. The array of nanofluidic channels 12 can be in fluid communication with the output chamber 14. Sample molecules or particles of interest 18 can be disposed in the array of nanofluidic channels 10. Control or comparative molecules or particles of interest 18 can be disposed in the array of nanofluidic channels 10. In some embodiments, the array of nanofluidic channels 12 connect the input chamber 10 to the output chamber 14. In some embodiments, sample molecules or particles of interest 18 and control or comparative molecules or particles of interest 20 are loaded into the sample input chamber, and travel in buffer solution 16 through the array of nanofluidic channels. In some embodiments, the sample molecules or particles of interest 18 and control or comparative molecules or particles of interest 20 are deposited from the array of nanofluidic channels 12 into the sample output chamber 14.

Figure 2:
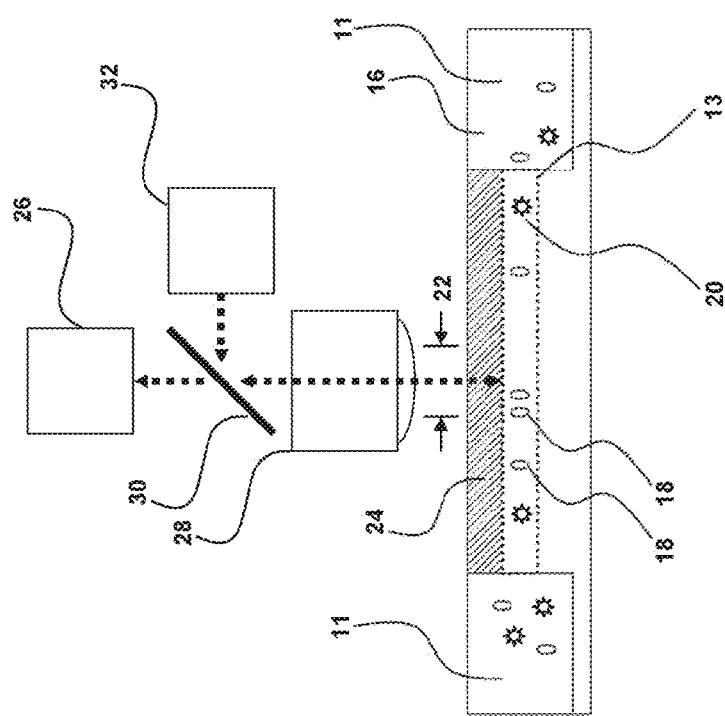
FIG. 2 is a schematic diagram illustrating an embodiment of an imaging setup to detect signals emitted from labeled molecules or particles to tabulate the amount, intensity, and configuration of the sample and reference molecule or particles.

FIG. 2 is a schematic diagram illustrating an arrangement for detection of sample molecules or particles of interest according to some embodiments herein. In some embodiments, the arrangement comprises a first sample inlet or outlet 11, a second sample inlet or outlet 11, and at least one fluidic channel 13 positioned therebetween and in fluid communication with each of the first and second inlet or outlet 11. It is contemplated herein that if a sample is loaded into the first inlet or outlet 11, the first inlet or outlet 11 functions as an inlet and the second inlet or outlet 11 can function as an outlet. It is contemplated herein that if a sample is loaded into the second inlet or outlet 11, the second inlet or outlet 11 functions as an inlet and the first inlet or outlet 11 can function as an outlet. In some embodiments, the sample comprises molecules or particles of interest 18, control or comparative particles of interest 20, or a combination of the two. In some embodiments, the molecules or particles of interest 18, control or comparative particles of interest 20 travel through the fluidic channel 13. In some embodiments, the fluidic channel 13 comprises a nanochannel. In some embodiments, the fluidic channel 13 comprises a microchannel. In some embodiments, the fluidic channel 13 comprises a detection region 22. In some embodiments, the system comprises a cover 24 disposed over the detection region 24. In some embodiments, the cover 24 comprises a transparent cap. In some embodiments, a detector 26 is positioned over the detection region 22 and the cover 24 (if present). In some embodiments, for example, if optical detection is used, the detector 26 comprises a photon detection/imager. In some embodiments, a lens 28 is positioned in optical communication with the detection region 22 and detector 26. In some embodiments, the lens 28 is positioned between detection region 22 and detector 26. In some embodiments, a dichroic mirror 30 is positioned in an optical communication with the detection region 22, lens 28, detector 26, and an excitation source 32, so that a fluorescent label, if present, can be excited, and fluorescence from the fluorescent label, if present, can be detected.

In some embodiments, the comparison of samples to a reference sample is provided in the form of a histogram. In some embodiments, physical counts of molecules with a particular labeling pattern that matches to a reference or de novo genomic assembly in silico are tabulated in a histogram distribution to reflect coverage depth. A higher or lower than average coverage depth in specific region or entire chromosome reflects the deviation from normal ploidy such as in the case of aneuploidy in genetic disorder or structural variations in cancer

ADDITIONAL ALTERNATIVE EMBODIMENTS

Some embodiments described herein can include the following: A method of characterizing a sample, comprising:

labeling a region of sample molecules with at least two labels; translocating the labeled sample molecules through a fluidic channel, wherein the fluidic channel is configured to elongate at least a portion of the sample molecule, and wherein the fluidic channel has a length of at least 10 nm and a cross-sectional diameter of less than 5000 nm; detecting signals arising from the labeled samples in the fluidic channels; and correlating the signals arising from the labeled samples to signals arising from the corresponding region of a reference molecule. The method can further comprise: labeling a region of the reference molecule corresponding to the region of the sample molecules; translocating the labeled reference sample molecule through a fluidic channel, wherein the fluidic channel is configured to elongate at least a portion of the sample molecule, and wherein the fluidic channel has a length of at least 10 nm and a cross-sectional diameter of less than 5000 nm; and detecting signals arising from the labeled reference sample in the fluidic channels, wherein the signals arising from a known corresponding region of a reference molecule are the signals arising from the labeled reference sample.

In some embodiments, a method of characterizing a sample is provided. The method can comprise: labeling sample nucleic acid molecules; translocating the labeled sample nucleic acid molecules through a fluidic nanochannel, wherein the fluidic nanochannel is configured to elongate at least a portion of the sample nucleic acid molecules, and wherein the fluidic nanochannel has a length of at least 10 nm and a cross-sectional diameter of less than 1000 nm; detecting signals arising from the sample nucleic acid molecules in the fluidic channels; determining the positions of the labels on the sample nucleic acid molecules; and aligning the positions of the labels on the sample nucleic acid molecules to the position of labels in a reference genome.

In some embodiments, a method of characterizing a sample is provided. The method can comprise: processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap; incorporating one or more bases into the double-stranded DNA so as to eliminate at least a portion of the gap; labeling at least a portion of the processed double-stranded DNA with one or more tags; and quantifying the signal arising from the labels on the double-stranded DNA; comparing the quantity of the signal arising from the double-stranded DNA to the quantity of the signal arising from a reference DNA; and determining the presence of a genetic abnormality in the double-stranded DNA when the quantity of the signal arising from the double-stranded DNA differs from the quantity of the signal arising from the reference DNA.

In some embodiments, a method of characterizing a sample is provided. The method can comprise labeling a plurality of sequence-specific locations on a sample DNA; linearizing at least a portion of the sample DNA; quantifying the signal arising from the labels on the sample DNA; comparing the quantity of the signal arising from the sample DNA to the quantity of the signal arising from a reference DNA; and determining the presence of a genetic abnormality in the sample DNA when the quantity of the signal arising from the sample DNA differs from the quantity of the signal arising from the reference DNA.

In some embodiments, a system for characterizing a sample is provided. The system can comprise: one or more regions for labeling sample molecules with at least two labels; a fluidic channel for translocating the labeled sample molecules, wherein the fluidic channel is configured to elongate at least a portion of the sample molecule, and wherein the fluidic channel has a length of at least 10 nm and a cross-sectional diameter of less than 5000 nm; and a device for detecting signals arising from the labeled samples in the fluidic channels.

In some embodiments, a system for characterizing a sample is provided. The system can comprise: one or more regions for labeling sample nucleic acid molecules; a fluidic nanochannel for translocating the labeled sample nucleic acid molecules, wherein the fluidic nanochannel is configured to elongate at least a portion of the sample nucleic acid molecules, and wherein the fluidic nanochannel has a length of at least 10 nm and a cross-sectional diameter of less than 1000 nm; and a device for detecting signals arising from the sample nucleic acid molecules in the fluidic channels.

In some embodiments, a system for characterizing a sample is provided. The system can comprise: one or more regions for processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap; one or more regions for incorporating one or more bases into the double-stranded DNA so as to eliminate at least a portion of the gap; one or more regions for labeling at least a portion of the processed double-stranded DNA with one or more tags; and a device for quantifying the signal arising from the labels on the double-stranded DNA.

In some embodiments, a system for characterizing a sample is provided. The system can comprise: a region for labeling a plurality of sequence-specific locations on a sample DNA; a region for linearizing at least a portion of the sample DNA; and a device for quantifying the signal arising from the labels on the sample DNA.

In some embodiments, a system for characterizing a sample is provided. The system can comprise: means for labeling sample molecules with at least two labels; means for linearizing the labeled sample molecules; and means for detecting signals arising from the labeled samples in the fluidic channels.

In some embodiments, a system for characterizing a sample is provided. The system can comprise: means for labeling sample nucleic acid molecules; means for linearizing the labeled sample nucleic acid molecules; and means for detecting signals arising from the sample nucleic acid molecules in the fluidic channels.

In some embodiments, a system for characterizing a sample is provided. The system can comprise: means for processing double-stranded DNA samples so as to give rise to a flap of the first strand of the double-stranded DNA samples being displaced from the double-stranded DNA samples, wherein the flap has a length in the range of from about 1 to about 1000 bases, and wherein the flap gives rise to a gap in the first strand of the double-stranded DNA samples corresponding to the flap; means for incorporating one or more bases into the double-stranded DNA so as to eliminate at least a portion of the gap; means for labeling at least a portion of the processed double-stranded DNA with one or more tags; and means for quantifying the signal arising from the labels on the double-stranded DNA.

In some embodiments, a system for characterizing a sample is provided. The system can comprise: system for characterizing a sample, comprising: means for labeling a plurality of sequence-specific locations on a sample DNA; means for linearizing at least a portion of the sample DNA; and means for quantifying the signal arising from the labels on the sample DNA.

According to some embodiments, a method or system as described herein is provided, wherein the sample is selected from the group consisting of a bacteria, a virion, a DNA molecule, an RNA molecule, a nucleic acid polymer, a protein, a peptide, and a polysaccharide.

According to some embodiments, a method or system as described herein is provided, wherein the sample is derived from maternal blood, and wherein the reference molecule is derived from a maternal sample other than blood.

According to some embodiments, a method or system as described herein is provided, wherein the sample comprises a nucleotide, and wherein the at least two labels are located at either end of a zone of interest in the nucleotide.

According to some embodiments, a method or system as described herein is provided, wherein the label is selected from the group consisting of a fluorescent label, a radioactive label, a magnetic label, or a combination thereof.

According to some embodiments, a method or system as described herein is provided, wherein the optical inspection comprises determining the physical count, the intensity, the wavelength, or the size of the labels.

According to some embodiments, a method or system as described herein is provided, wherein the optical inspection comprises determining the length of at least one labeled region in the sample.

According to some embodiments, a method or system as described herein is provided, wherein correlating the signals comprises determining the signals arising from a pool of samples or a pool of portions of a sample.

According to some embodiments, a method or system as described herein is provided, wherein correlating the signals comprises using the ratio (K) between the signal arising from a plurality of samples or sample portions (S1, S2 . . . Sn) and the signal arising from the reference (C): K1=S1/C, K2=S2/C . . . Kn=Sn/C. In some embodiments, a difference between K1 and Kn is used to identify the presence of a fetal sample. In some embodiments, a difference between K1 and Kn is used to identify the presence of DNA from a tumor or other cancer source. In some embodiments, a difference between K1 and Kn is used to determine the presence of a genetic abnormality in the sample. In some embodiments, the genetic abnormality is aneuploidy. In some embodiments, the genetic abnormality is a translocation, addition, amplification, transversion, or inversion. In some embodiments, the reference is derived from a known diploid or haploid chromosome. In some embodiments, the signals from the sample are correlated with the population distribution from a metagenomic or microbiome study.

According to some embodiments, a method or system as described herein is provided, in which the fluidic channel is a nanochannel. In some embodiments, the fluidic channel is disposed parallel to a surface of a substrate. In some embodiments, According to some embodiments, a method or system as described herein is provided, further comprising generating a histogram distribution to reflect coverage depth for the sample.

According to some embodiments, a method or system as described herein is provided, wherein the sample comprises circulating fetal cells, circulating tumor cells, or body fluids or tissues.

According to some embodiments, a method or system as described herein is provided, wherein the translocating comprises subjecting the labeled sample to a motivating force selected from the group consisting of a fluid flow, a radioactive field, an electroosmotic force, an electrophoretic force, an electrokinetic force, a temperature gradient, a surface property gradient, a capillary flow, a pressure gradient, a magnetic field, an electric field, a receding meniscus, a surface tension, a thermal gradient, a pulling force, a pushing force, and a combination thereof.

According to some embodiments, a kit for performing a method as described herein is provided.

According to some embodiments, a kit for using the system of any one of the preceding claims is provided.

In the description provided herein, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Unless defined otherwise, technical and scientific terms used herein have the same meaning as commonly understood by one of ordinary skill in the art to which this invention belongs.

As used herein, the term "channel" means a region defined by borders. Such borders may be physical, electrical, chemical, magnetic, and the like. The term "nanochannel" is used to clarify that certain channels are considered nanoscale in certain dimensions.

As used herein, the term "DNA" refers to DNA of any length (e.g., 0.1 Kb to 1 megabase). The DNA can be a highly pure preparation, crude, or semi crude material. The DNA can come from any biological source or can be synthetic.

As used herein, the term "nucleotide" refers to a molecule containing deoxyribonucleic acids (e.g., DNA, mtDNA, gDNA, or cDNA), ribonucleic acid (e.g., RNA or mRNA), or any other variant of nucleic acids known in the art. The term "labeled nucleotide" refers to a nucleotide comprising any modification that is detectable. This includes but is not limited to nucleotides with reporter groups attached to the base. Reporter groups include but are not limited to fluorescent dyes, haptens, biotin molecules or gold nanoparticles. The term "native nucleotide" refers to a nucleotide that is not modified, or has a slight modification that does not interfere with its incorporation into DNA. The terms "t", "C", "a", "g" and "u" refer to nucleotides in DNA.

The term "nick" refers to a phosphodiester bond break occurring on one DNA strand or the other, having a 3' hydroxyl end.

As used herein, the term "nicking endonuclease" refers to any enzyme, naturally occurring or engineered, that is capable of breaking a phosphodiester bond on a single DNA strand leaving a 3'-hydroxylat a defined sequence. Nicking endonucleases can be naturally occurring, engineered by modifying restriction enzymes to eliminate one DNA strand cutting activity, or produced by fusing a nicking subunit to a DNA binding domain, for example, zinc fingers and transcription activator like effectors DNA recognition domains.

As used herein, the term "labeling sites" refers to any DNA site with an exposed 3' hydroxyl group onto which the polymerase can add nucleotides in a template dependent manner. Labeling sites can be generated by nicking endonucleases, hybridized probes, or any chemical or physical means of breaking a phosphodiester bond on any one DNA strand. Means of breaking a phosphodiester bond can occur to DNA outside its biological source or prior to DNA extraction, for example as a result of a biological sample exposure to chemicals, and external forces such as radiation. If 3' ends are not extendable, repair can be performed to restore the hydroxyl group, for example by using New England Biolabs' PreCR kit.

As used herein a "sample" can include, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein, the term "chromosome" refers to the heredity-bearing gene carrier of a living cell which is derived from chromatin and which comprises DNA and protein components (especially histones).

As one of skill in the art will recognize, "translocating" can be used interchangeably with linearizing when used in the context passing a DNA molecule through a nanochannel.

The methods, apparatuses, systems, and kits described herein can incorporate the methods, apparatuses, systems, and kits described in any of the following references: U.S. Patent Application Publication No. 2009/0305273; PCT Publication No. WO/2008/079169; U.S. Patent Application Publication No. 2008/0242556; PCT Publication No. WO/2008/121828; U.S. Patent Application Publication No. 2011/0171634; PCT Publication No. WO/2010/002883; U.S. Patent Application Publication No. 2011/0296903; PCT Publication No. WO/2009/149362; U.S. Patent Application Publication No. 2011/0306504; PCT Publication No. WO/2010/059731; U.S. Patent Application Publication No. 2012/0097835; PCT Publication No. WO/2010/135323; PCT Application No. PCT/US11/57115; U.S. patent application Ser. No. 13/606,819; PCT Application No. PCT/US2012/054299; U.S. Patent Application Publication No. 2012/0244635; PCT Publication No. WO/2011/038327; U.S. Patent Application Publication No. 2012/0237936; U.S. patent application Ser. No. 13/503,307; PCT Publication No. WO/2011/050147; U.S. Patent Application Ser. No. 61/734,327; U.S. Patent Application Ser. No. 61/761,189; and U.S. Patent Application Ser. No. 61/713,862, which are each hereby incorporated by reference in their entireties.

EXAMPLE 1

Genomic fragments from a human male sample were generated by PCR, labeled, and run through a nanochannel. Detected fragments were then aligned to a single gene reference optical map for each chromosome. The molecules were sorted based on the alignment start site.

Figure 7A:
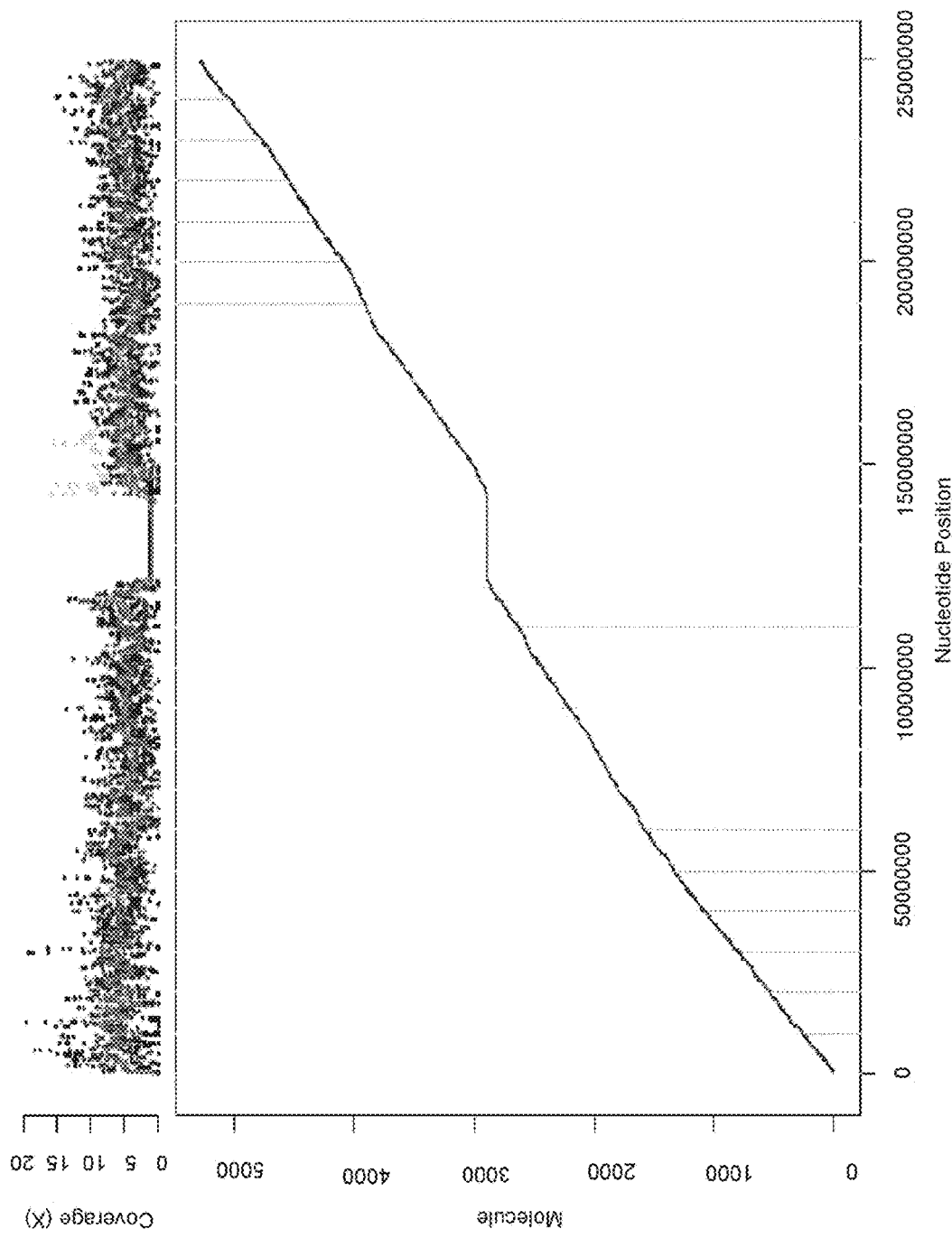
FIG. 7A is a graph illustrating diploid genomic fragments from a human male sample aligned to chromosome 1. The y-axis provides the quantity of coverage. The x-axis provides the nucleotide position. The average coverage depth was 5X.

As shown in FIG. 7A, the average coverage depth observed for a diploid autosomal chromosome (chromosome 1) was 5X, and was evenly distributed across the chromosome. If the sampling of molecules had been even, the alignment start sites would have been randomly distributed across the chromosome, resulting in a linear plot.

Figure 7B:
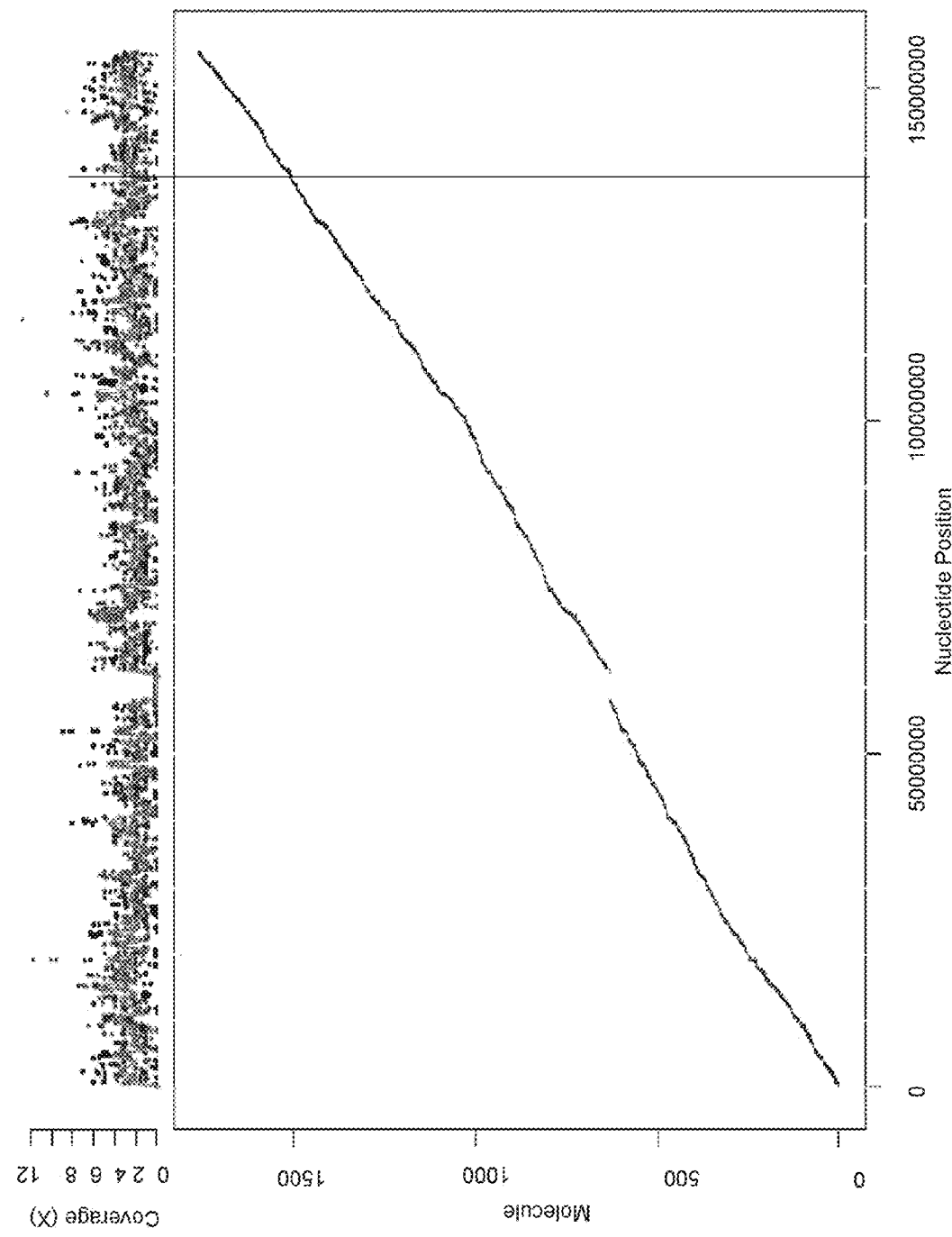
FIG. 7B is a graph showing a haploid sex chromosome X from the same male sample shown with an average coverage depth of 2X-2.5X (roughly half of the depth of diploid autosomes), demonstrating the quantitative measurement using the methods and platform according to some embodiments herein.

As shown in FIG. 7B, the average coverage depth observed for a haploid sex chromosome (chromosome X) from the same male sample was 2X-2.5X (roughly half the depth of diploid autosomes), and was also evenly distributed across the chromosome. This example demonstrates the quantitative measurements that can be achieved using the methods and platform described herein.

What is claimed is:

1. A method of detecting a tumor cell in a sample comprising polynucleotide sequences, the method comprising:
   labeling a plurality of sequence-specific locations on a polynucleotide sequence of a sample molecule of less than 1000 nucleotides in length;
   linearizing at least a portion of the sample molecule in a fluidic nanochannel,
   wherein the fluidic nanochannel has a length of at least 10 nm and cross sectional diameter of less than 1000 nm;
   quantifying a signal from the labels on the sample molecule; and
   comparing a quantity of the signal from the sample molecule to a quantity of signal from a reference molecule of less than 1000 nucleotides in length, wherein a difference between the signal of the sample molecule and the signal of the reference molecule is indicative of the presence or absence of a tumor cell in the sample.

2. The method of claim 1, wherein the sample is derived from a tumor cell, suspected of comprising circulating tumor cells, or derived from a tissue in fluid communication with a tumor cell.

3. The method of claim 1, wherein the reference molecule is from a healthy cell.

4. The method of claim 1, wherein the quantity of the signal comprises coverage depth.

5. The method of claim 4, further comprising generating a histogram distribution to reflect coverage depth for the sample.

6. The method of claim 1, wherein the sample molecule and the reference molecule are from different tissues of the same organism.

7. The method of claim 1, wherein the labeling comprises labeling the sample molecule with at least two labels located at either end of a zone of interest in the sample molecule.

8. The method of claim 1, wherein the quantity of signal from the reference molecule comprises an electronically or optically stored value or set of values.

9. The method of claim 1, wherein comparing the quantity of the signal from the sample molecule to the quantity of signal from the reference molecule comprises generating a histogram distribution to reflect coverage depth for the sample.

10. The method of claim 1, wherein comparing the quantity of the signal from the sample molecule to the quantity of signal from the reference molecule comprises using the ratio (K) between the signal arising from a plurality of samples or sample portions (S1, S2 . . . Sn) and the signal arising from the reference molecule (C):

$$K1=S1/C, K2=S2/C \ldots Kn=Sn/C.$$

11. The method of claim 10, wherein a difference between K1 and Kn is used to determine the presence of a tumor cell in the sample.

12. The method of claim 1, wherein the polynucleotide sequence of the sample molecule comprises less than 550 nucleotides in length.

13. A system for detecting a tumor cell in a sample, comprising:
- a fluidic nanochannel for translocating labeled sample nucleic acid molecules of less than 1000 nucleotides in length, wherein the fluidic nanochannel has a length of at least 10 nm and cross sectional diameter of less than 1000 nm, wherein the fluidic nanochannel is configured to elongate at least a portion of the labeled sample nucleic acid molecules, and wherein the sample nucleic acid molecules are labeled while being less than 1000 nucleotides in length; and
- a device configured to detect physical counts of signals arising from the labeled sample nucleic acid molecules of less than 1000 nucleotides in length in the fluidic channels.

14. The system of claim 13, wherein the sample comprises circulating tumor cells, body fluids, or tissues, or is suspected of comprising circulating tumor cells.

15. The system of claim 13, wherein the system is configured to correlate signals arising from the labeled sample nucleic acid molecules to signals arising from the corresponding region of a reference molecule.

16. The system of claim 13, wherein the signals arising from a known corresponding region of a reference molecule are the signals arising from a labeled reference molecule.

17. The system of claim 13, wherein correlating the signals comprises determining the signals arising from a pool of samples or a pool of portions of a sample.

18. The system of claim 13, wherein the system is configured to correlate the signals comprises using the ratio (K) between the signal arising from a plurality of samples or sample portions (S1, S2 . . . Sn) and the signal arising from the reference (C):

$$K1=S1/C, K2=S2/C \ldots Kn=Sn/C.$$

19. The system of claim 18, wherein a difference between K1 and Kn is used to determine the presence of a nucleic acid from a tumor cell in the sample.

20. The system of claim 13, wherein the system is configured to generate a histogram distribution to reflect coverage depth for the sample.

21. The system of claim 13, wherein the detecting comprises optical inspection comprising determining the physical count, the intensity, the wavelength, or the size of the labels, and wherein the detecting comprises optical inspection comprising determining the length of at least one labeled region in the sample.

* * * * *